United States Patent [19]

Kaneko et al.

[11] Patent Number: 5,416,066

[45] Date of Patent: May 16, 1995

[54] 1,4-BENZOTHIAZEPINE DERIVATIVES

[75] Inventors: Noboru Kaneko, Tokyo; Tatsushi Oosawa, Gunma; Teruyuki Sakai, Gunma; Hideo Oota, Gunma, all of Japan

[73] Assignee: Kirin Brewery Co., Ltd., Tokyo, Japan

[21] Appl. No.: 81,254

[22] PCT Filed: Dec. 27, 1991

[86] PCT No.: PCT/JP91/01804

§ 371 Date: Jun. 25, 1993

§ 102(e) Date: Jun. 25, 1993

[87] PCT Pub. No.: WO92/12148

PCT Pub. Date: Jul. 23, 1992

[30] Foreign Application Priority Data

Dec. 28, 1990 [JP] Japan ................................. 2-416066

[51] Int. Cl.$^6$ ................. C07D 417/06; C07D 417/14; A61K 31/55

[52] U.S. Cl. ..................................... 514/211; 540/490

[58] Field of Search ...................... 540/490; 514/211

[56] References Cited

U.S. PATENT DOCUMENTS

| | | | |
|---|---|---|---|
| 3,794,639 | 2/1974 | Krapcho et al. | 540/490 |
| 5,158,947 | 10/1992 | Tatsuoka | 514/211 |
| 5,250,679 | 10/1993 | Blackburn | 514/211 |

FOREIGN PATENT DOCUMENTS

| | | |
|---|---|---|
| 107930 | 5/1984 | European Pat. Off. |
| 444924 | 9/1991 | European Pat. Off. |
| 59-93047 | 5/1984 | Japan |
| 61-40651 | 10/1986 | Japan |

OTHER PUBLICATIONS

Journal of Tokyo Women's Medical College, 52, 1443 (1982).
Czollner et al Chemical Abstracts, vol. 111, No. 11, Abstract No. 97194n (1988).
Krapcho et al Chemical Abstracts, vol. 68, No. 19, Abstract No. 87285X (1968).

*Primary Examiner*—Mark L. Berch
*Attorney, Agent, or Firm*—Scully, Scott, Murphy & Presser

[57] ABSTRACT

An object of the invention is to provide compounds having a myocardial KD (Kinetic cell death)-inhibiting effect without being accompanied by a cardiodepressant effect.

A 1,4-benzothiazepine derivative represented by the following Formula [I]:

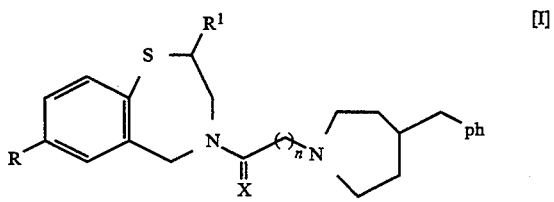

wherein each of substituent groups is defined as follows: R represents H or a $C_1$–$C_3$ lower alkoxy group; X represents O or $H_2$; n represents 1 or 2; $R^1$ represents H, a substituted phenyl group wherein the substituent group is OH or a $C_1$–$C_3$ lower alkoxy group,

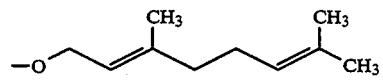

a $C_1$–$C_3$ lower alkoxy group,

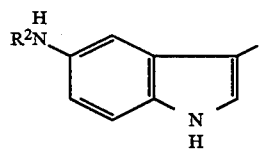

wherein $R^2$ represents a $C_1$–$C_3$ acyl group, and ph represents a phenyl group, or a pharmaceutically acceptable salt thereof.

19 Claims, No Drawings

1,4-BENZOTHIAZEPINE DERIVATIVES

This application is a 371 of PCT/JP91/01804.

TECHNICAL FIELD

This invention relates to novel 1,4-benzothiazepine derivatives, in particular novel 1,4-benzothiazepine derivatives having an effect of inhibiting overcontraction and overextension of the myocardium and protecting against myocardial necrosis without being accompanied by a cardiodepressant effect.

In addition, this invention relates to drugs containing the aforementioned novel 1,4-benzothiazepine derivatives as an effective ingredient which work on the circulatory system, in particular the 1,4-benzothiazepine derivatives containing the novel 1,4-benzothiazepine derivatives as an effective ingredient, which have an effect of inhibiting overcontraction and overextension of myocardium and protecting against myocardial necrosis without being accompanied by a cardiodepressant effect.

PRIOR ART

The recent increase in the average age of the population has been accompanied by an increase in circulatory diseases, such as hypertension, angina and myocardial infarction. In particular, there have been many sudden occurrences of myocardial infarction with a high mortality rate. Hitherto, the cause of this myocardial infarction has been attributed to obstruction, by thrombus or coronary spasm, of the coronary artery which supplies nutrition to the heart. Recently, however, Kaneko et al. have proposed a new mechanism for myocardial infarction, according to which the myocardia of myocardial infarction patients exhibit two forms of necrosis, Static Cell Death (hereinafter referred to as SD) and Kinetic Cell Death (hereinafter referred to as KD), with KD being the main cause of myocardial infarction (Journal of Tokyo Women's Medical College, 52, 1443, 1982). In addition, Kaneko et al. have reported using a rabbit to create a model of a myocardial infarction caused by KD, and using calcium antagonists to inhibit the symptoms thereof (refer to Japanese Patent Publication No. Sho 61-40651). Moreover, they have recently succeeded in creating a model of a myocardial infarction caused by KD in a Langendorff in vitro system using an isolated rat heart, and by using this model they have found that some Ca antagonists have a KD-inhibiting effect similar to that found the in vivo system. However, some of these Ca antagonists have a strong cardiodepressant effect, and it was thought desirable to develop compounds having a weak cardiodepressant effect, and a strong KD-inhibiting effect.

DISCLOSURE OF THE INVENTION

It is an object of this invention to provide compounds having a KD-inhibiting effect without being accompanied by a cardiodepressant effect and novel 1,4-benzothiazepine derivatives, in particular novel 1,4-benzothiazepine derivatives having specific substituent groups and pharmaceutically acceptable salts thereof.

In addition, it is an object of this invention to provide drugs for the prevention of myocardial necrosis and for the prevention and treatment of acute myocardial infarction in which the above-mentioned novel 1,4-benzothiazepine derivatives having specific substituent groups and pharmaceutically acceptable salts thereof are contained as an effective ingredient.

The above object of this invention is accomplished by 1,4-benzothiazepine derivatives and pharmaceutically acceptable salts thereof.

Namely, the compounds of this invention are 1,4-benzothiazepine derivatives represented by the following Formula [I]:

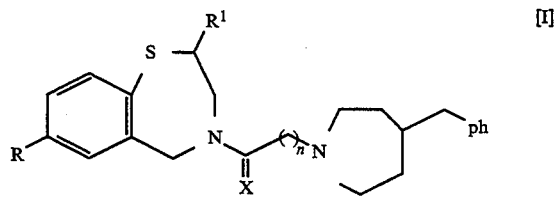

wherein each of substituent groups is defined as follows: R represents H or a $C_1$–$C_3$ lower alkoxy group; X represents O or $H_2$; n represents 1 or 2; $R^1$ represents H, a substituted phenyl group wherein the substituent group is OH or a $C_1$–$CH_3$ lower alkoxy group,

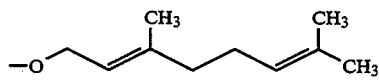

a $C_1$–$C_3$ lower alkoxy group or

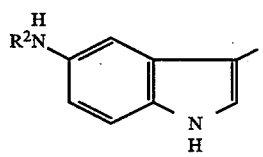

wherein $R^2$ represents a $C_1$–$C_3$ acyl group and ph represents a phenyl group, or pharmaceutically acceptable salts thereof.

The ability to produce a strong KD-inhibiting effect without being accompanied by a cardiodepressant effect is a new property discovered in the novel 1,4-benzothiazepine compounds of this invention.

The compound represented by Formula [I] has basic nitrogen atoms and it is thus possible to form an acid addition salt at this site. The acid used to form the acid addition salt should be selected from pharmaceutically acceptable acids. Consequently, the pharmaceutically acceptable salts of the compound shown in Formula [I] also fall within the scope of the compounds according to this invention. Salts can include, for example, inorganic acid salts such as hydrochloride, sulfate or the like and organic acid salts such as citrate, maleate, fumarate, benzoate, succinate, acetate, tartrate, malate or the like.

The drugs of this invention for the prevention of myocardial necrosis and for the prevention and treatment of acute myocardial infarction contain as an effective ingredient one or more of the 1,4-benzothiazepine derivatives represented by Formula [I] or pharmaceutically acceptable salts thereof.

The novel 1,4-benzothiazepine derivatives and pharmaceutically acceptable salts of this invention have a strong myocardial necrosis-inhibiting effect without being accompanied by a cardiodepressant effect, can be used as an excellent drug for the prevention of myocardial necrosis and an excellent drug for the prevention and treatment of acute myocardial infarction. Consequently, this invention can provide an excellent drug for the prevention of myocardial necrosis and an excellent drug for the prevention and treatment of acute myocardial infarction.

Preparation of 1,4-benzothiazepine derivatives

The compounds of Formula [I] of this invention can be prepared according to various routes; for example, by following the reaction scheme of the following Routes A), to E), provided that R, $R^1$, X, n and ph in the reaction formulae are as defined in Formula [I].

Route A): This Route is generally shown as follows.

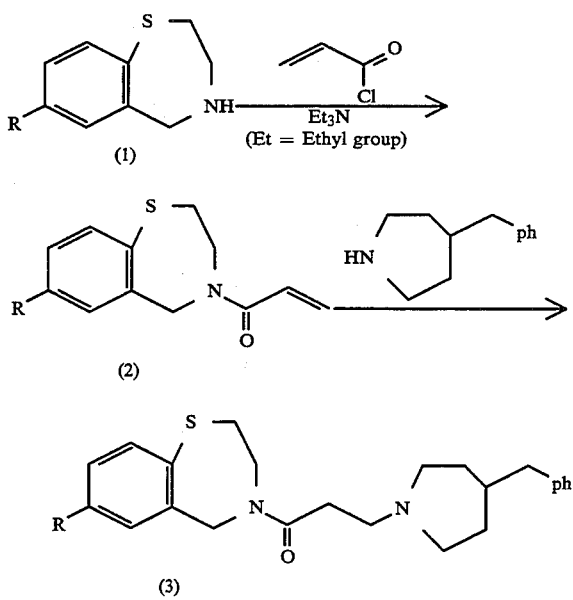

Compound (1) is reacted with acryloyl chloride in the presence of a base of triethylamine, di-isopropyl ethylamine or the like in a non-protonic solvent of methylene chloride, chloroform, tetrahydrofuran (THF) or the like, preferably at 0° C. to room temperature to live an amide compound (2). The amide compound (2) is reacted with 4-benzyl piperidine in a solvent of methylene chloride, chloroform, methanol, ethanol, THF or the like at room temperature to give compound (3) of this invention. The product is isolated and purified by conventional methods.

Route B): This Route is generally shown as follows.

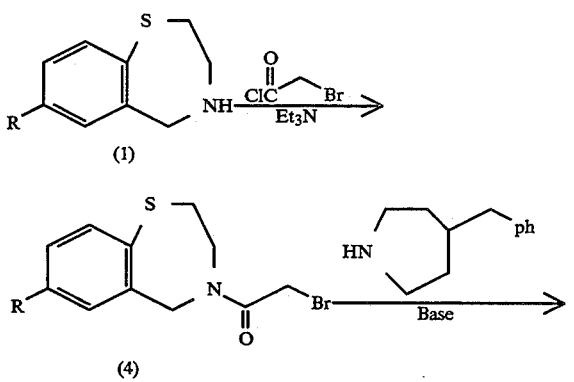

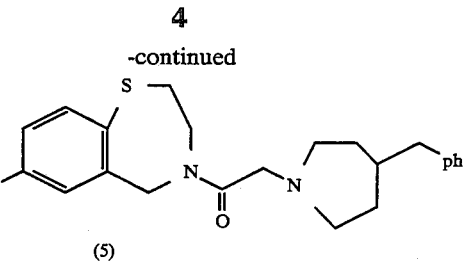

Compound (1) is reacted with bromoacetyl chloride in the presence of a base of triethylamine or the like in a non-protonic solvent of methylene chloride, chloroform, THF or the like, preferably at 0° to room temperature to give an amide compound (4). The amide compound (4) is heated at reflux with 4-benzyl piperidine in the presence of a base of potassium carbonate, sodium carbonate, potassium hydroxide, sodium hydroxide or the like in a solvent of acetonitrile, methyl ethyl ketone, acetone or the like, to give compound (5) of this invention. The product is isolated and purified by conventional methods.

Route C): This Route is generally shown as follows.

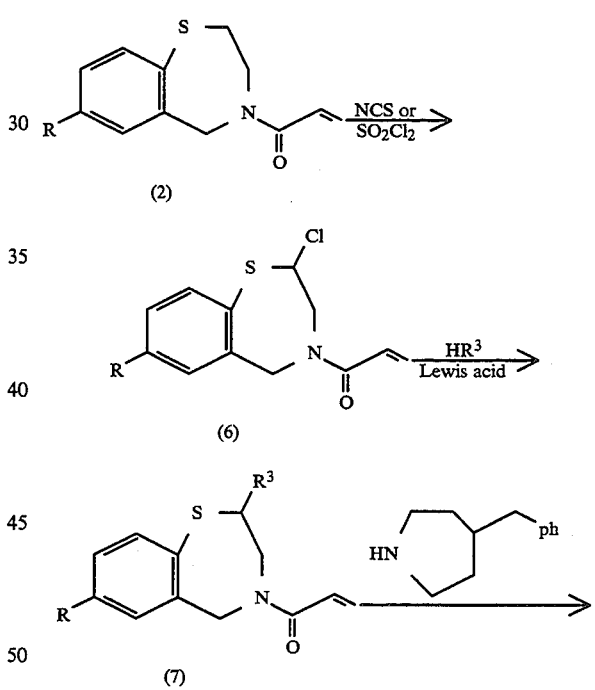

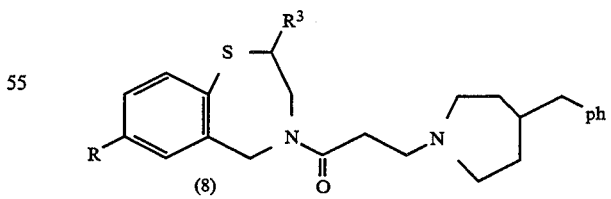

wherein $R^3$ represents the same as the above $R^1$ exclusive of H.

This Route comprises three reaction steps. In the first step, a starting material (2) is chlorinated at 2-position thereof. The amide compound (2) is heated at reflux in the presence of imide N-chlorosuccinate (NCS) in a suitable non-protonic solvent, preferably toluene, or is reacted with sulfuryl chloride in a non-protonic solvent of methylene chloride, chloroform or the like at 0° C. to room temperature, preferably at 0° C., to give a chloro compound (6). Then, the compound (6) is reacted with a Lewis acid of stannic chloride, zinc chloride, aluminum chloride or the like in the presence of an indole derivative, substituted benzene derivative, alcohol or the like in a non-protonic solvent of methylene chloride, acetonitrile or the like, preferably at 0° C. to room temperature to give a compound (7). This compound (7) is reacted with 4-benzyl piperidine in the same manner as in the above-mentioned Route A) to give compound (8) of this invention. The product is isolated and purified by conventional methods.

Route D): This Route is generally shown as follows.

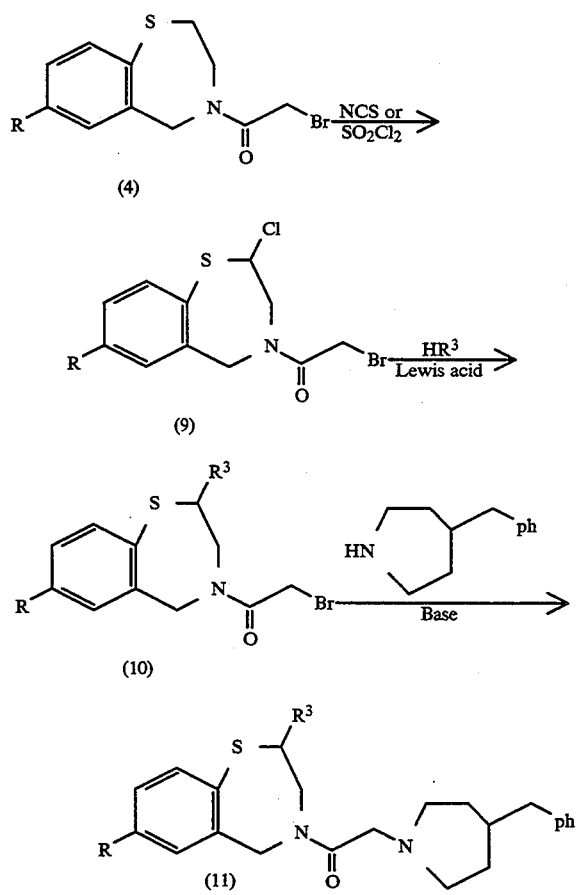

This Route comprises three reaction steps in the same manner as in the above-mentioned Route C). In the first step, a compound (4) is chlorinated. The amide compound (4) is heated at reflux in the presence of imide N-chlorosuccinate (NCS) in a suitable non-protonic solvent, preferably toluene, or is reacted with sulfuryl chloride in a non-protonic solvent of methylene chloride, chloroform or the like at room temperature, to give a chloro compound (9). The compound (9) is reacted with a Lewis acid of stannic chloride, zinc chloride, aluminum chloride or the like in the presence of an indole derivative, substituted benzene derivative, alcohol or the like in a non-protonic solvent of methylene chloride, acetonitrile or the like, preferably at 0° C. to room temperature to give a compound (10). This compound (10) is reacted with 4-benzyl piperidine in the presence of a base of potassium carbonate, sodium carbonate or the like in the same manner as in the above-mentioned Route B), to give compound (11) of this invention. The product is isolated and purified by conventional methods.

Route E): This Route is generally shown as follows.

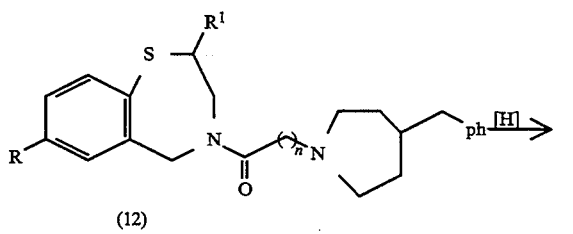

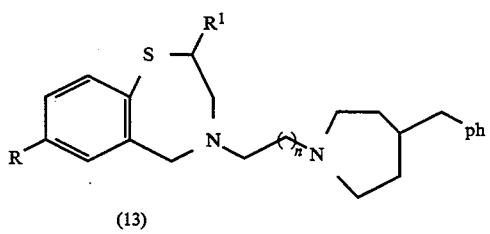

In this reaction, an amide compound (12) is reacted in the presence of a suitable reducing agent selected from, for instance, aluminum lithium hydride, methoxy ethoxy aluminum sodium hydride and diborane, in a non-protonic solvent, preferably THF, preferably at 0° C. to room temperature, or is heated at reflux, to give an amine compound (13). The product is isolated and purified by conventional methods.

The compounds of this invention which can be prepared as mentioned above can be converted by conventional methods into the form of the acid addition salts mentioned above. Utility of the compounds of this invention The 1,4-benzothiazepine derivatives of Formula [I] of this invention and the pharmaceutically acceptable salts thereof have a KD-inhibiting effect as can be seen from the results of pharmacological testing as mentioned below and can be useful as drugs for curing circulatory disease. Specifically, the derivatives are useful as drugs for anti-myocardial infarction, particularly as drugs for prevention or treatment of acute myocardial infarction or inhibitors for myocardial necrosis.

In cases where the compounds of this invention are used as drugs for prevention or treatment of acute myocardial infarction, the dosage thereof varies depending on the degree of disease, the patient's weight, method of administration or the like and is not particularly limited. Generally, the compounds can be orally or parenterally intravenously) administered approximately once a day in an amount of about 10 mg to 1,000 mg/day to an adult (average weight of 60 Kg). The administration form can include, for example, powder, parvule, granule, tablet, capsule, injection or the like. In addition, the preparation can be made by using a conventional carrier or diluent according to conventional methods.

The compounds according to this invention have a strong myocardial necrosis-inhibiting effect without being accompanied by a cardiodepressant effect. As a result, it is possible to provide an excellent drug for prevention or treatment of acute myocardial infarction. It should be appreciated that the fact of the compounds of this invention having the above-mentioned effect was unexpected to those skilled in the art.

EXAMPLE

This invention will be described concretely by the following experimental examples, but it is by no means restricted by these experimental examples unless exceeding the gist thereof.

(Preparation of the compounds)

Preparation examples of the compounds of this invention and physical and chemical properties thereof are as-follows. Moreover, measurement of NMR is made by using tetramethyl silane as an internal standard and the result is represented as ppm. "Part" in the examples shows part by volume.

Experimental Example 1

2,3,4,5-Tetrahydro-1,4-benzothiazepine (11 g) and triethylamine (13.5 g) were dissolved in THF (300 ml) and acryloyl chloride (9.5 g) was added dropwise thereto under ice cooling and agitated at room temperature for 30 minutes. A 10% potassium hydroxide aqueous solution was added thereto, agitated at room temperature and thereafter extracted with chloroform. The chloroform phase was washed with a saturated saline solution and dried on sodium sulfate and the solvent was distilled out under reduced pressure. Residue was purified by silica gel column chromatography (Wako Gel C-200, 200 g) and eluted with a mixed solvent of n-hexane (60 parts) +ethyl acetate (40 parts) to give 4-acryloyl-2,3,4,5-tetrahydro-1,4-benzothiazepine (12.59).

mp 108.5°–110.0° C. IR $\nu_{max}^{KBr}$(cm$^{-1}$): 1635, 1590 $^1$H-NMR(CDCl$_3$, 100 MHz)δ: 2.76–2.97 (2H, m), 3.99–4.23 (2H, m), 4.72–4.86 (2H, m), 5.57–5.79 (1H, m), 6.13–6.91 (2H, m), 7.12–7.68 (4H, m). FD-MS(m/z): 219 (M+).

Experimental Example 2

7-Methoxy-2,3,4,5-tetrahydro-1,4-benzothiazepine (10.0 g) (refer to preparation examples 1 to 6 as mentioned below), triethylamine (10.2 g) and acryloyl chloride (6.9 g) were reacted in the same manner as in Experimental Example 1 to give 4-acryloyl-7-methoxy-2,3,4,5-tetrahydro-1,4-benzothiazepine (10.6 g).

mp 79.0°–81.0° C. IR $\nu_{max}^{KBr}$(cm$^{-1}$): 1635, 1595. $^1$H-NMR(CDCl$_3$, 100 MHz)δ: 2.69–2.90 (2H, m), 3.80 (3H, s), 3.97–4.24 (2H, m), 4.67–4.82 (2H, m), 5.56–5.82 (1H, m), 6.10–7.53 (5H, m). FD-MS (m/z): 249 (M+).

Experimental Example 3

2,3,4,5-Tetrahydro-1,4-benzothiazepine (4.8 g), triethylamine (5.9 g) and bromoacetyl chloride (5.5 g) were reacted in the same manner as in Experimental Example 1 to give 4-bromoacetyl-2,3,4,5-tetrahydro-1,4-benzothiazepine (3.5 g).

IR $\nu_{max}^{CHCl_3}$(cm$^{-1}$): 1640. $^1$H-NMR(CDCl$_3$, 100 MHz)δ: 2.80–3.00 (2H, m), 3.78–4.18 (4H, m), 4.70–4.84 (2H, m), 7.15–7.65 (4H, m).

Experimental Example 4

7-Methoxy-2,3,4,5-tetrahydro-1,4-benzothiazepine (3.0 g), triethylamine (3.1 g) and bromoacetyl chloride (3.2 g) were reacted in the same manner as in Experimental Example 1 to give 4-bromoacetyl-7-methoxy-2,3,4,5-tetrahydro-1,4-benzothiazepine (2.5 g).

IR $\nu_{max}^{CHCl_3}$(cm$^{-1}$): 1640 $^1$H-NMR(CDCl$_3$, 100 MHz)δ: 2.75–2.94 (2H, m), 3.68–4.18 (4H, m), 3.80 (3H, s), 4.66–4.81 (2H, m), 6.65–7.58 (3H, m).

Experimental Example 5

4-Acryloyl-7-methoxy-2,3,4,5-tetrahydro-1,4-benzothiazepine (4.0 g) and 4-benzyl piperidine (3.7 g) were dissolved in chloroform (15 ml) and left to stand at room temperature for 2 days. The reaction mixture was purified by silica gel column chromatography (Wako Gel C-200, 150 g) and eluted with a mixed solvent of chloroform (98 parts)+methanol (2 parts) to give 4-[3-[1-(4-benzyl)piperidinyl]propionyl]-7-methoxy-2,3,4,5-tetrahydro-1,4-benzothiazepine (6.8 g) (compound (a)). This compound (1.0 g) was dissolved in methanol (10 ml) and a hydrogen chloridemethanol solution (10% (w/w), 2 ml) was added thereto to acidify. After distilling out the solvent, the residue was washed with ether to obtain a hydrochloride (0.95 g) in the form of powder.

IR $\nu_{max}^{KBr}$(cm$^{-1}$): 3400, 2920, 1635, 1590 (for hydrochloride) $^1$H-NMR(CDCl$_3$, 100 MHz)δ: 1.11–2.95 (17H, m), 3.78 (3H, s), 3.86–4.16 (2H, m), 4.65 (2H, s), 6.63–7.54 (8H, m). FD-MS (m/z): 424 (M+).

Experimental Example 6

4-Bromoacetyl-7-methoxy-2,3,4,5-tetrahydro-1,4-benzothiazepine (1.3 g) and 4-benzyl piperidine (0.9 g) were dissolved in acetonitrile (50 ml), potassium carbonate (1.1 g) was added thereto and the mixture was heated at reflux for 3 hours. After standing to cool, water was added thereto and extracted with chloroform. The chloroform phase was washed with a saturated saline solution and dried on sodium sulfate and the solvent was distilled out under reduced pressure. Residue was purified by silica gel column chromatography (Wako Gel C-200, 60 g) and eluted with a mixed solvent of chloroform (98 parts)+methanol (2 parts) to give 4-[1-(4-benzyl)piperidinyl]acetyl-7-methoxy-7,methoxy-2,3,4,5-tetrahydro-1,4-benzothiazepine (1.7 g).

IR $\nu_{max}^{CHCl_3}$(cm$^{-1}$) 1640 $^1$H-NMR(CDCl$_3$, 500MHz)δ: 1.14–2.09 (7H, m), 2.48–3.20 (8H, m), 3.79 (3H, s), 4.00–5.95 (4H, m), 6.65–7.50 (8H, m). FD-MS (m/z): 410 (M+).

Experimental Example 7

4-Acryloyl-2,3,4,5-tetrahydro-1,4-benzothiazepine (10 g) was dissolved in methylene chloride (150 ml) and sulfuryl chloride (9.3 g) was added thereto under ice cooling and agitated at 0° C. for 1 hour. To the reaction mixture water was added and extracted with chloroform. The chloroform phase was washed with a saturated saline solution and dried on sodium sulfate and thereafter the solvent was distilled out under reduced pressure. Residue was purified by silica gel column chromatography (Wako Gel C-200, 200 g) and eluted with a mixed solvent of n-hexane (70 parts)+ethyl acetate (30 parts) to give 4-acryloyl-2-chloro-2,3,4,5-tetrahydro-1,4-benzothiazepine (10.5 g).

mp 66.0°–68.0° C. IR $\nu_{max}^{KBr}$(cm$^{-1}$): 1640. $^1$H-NMR(CDCl$_3$, 100 MHz)δ: 4.05–4.15 (2H, m), 4.45–5.00 (2H, m), 5.01–5.22 (1H, m), 5.55–5.85 (1H, m), 6.15–6.85 (2H, m), 7.20–7.70 (4H, m).

Experimental Example 8

4-Acryloyl-7-methoxy-2,3,4,5-tetrahydro-1,4-benzothiazepine (4.0 g) and sulfuryl chloride (2.3 g) were reacted in the same manner as in Experimental Example 7 to give 4-acryloyl-2-chloro-7-methoxy-2,3,4,5-tetrahydro-1,4-benzothiazepine (2.4 g).

mp 97.5°–99.5° C. IR $\nu_{max}^{KBr}$(cm$^{-1}$): 1640. $^1$H-NMR(CDCl$_3$, 100 MHz)δ: 3.84 (3H, s), 4.13–4.23 (2H, m), 4.45–5.20 (3H, m), 5.60–5.85 (1H, m), 6.15–7.60 (6H, m).

Experimental Example 9

The above-mentioned 4-acryloyl-2-chloro-2,3,4,5-tetrahydro-1,4-benzothiazepine (2.9 g) and 5-(acetamide) indole (2.5 g) were dissolved in acetonitrile (80 ml) and zinc chloride (4.8 g) was added thereto at room temperature and agitated at that temperature for 4 hours. To the reaction mixture water was added and extracted with chloroform. The chloroform phase was washed with a saturated saline solution and dried on sodium sulfate and thereafter the solvent was distilled out under reduced pressure. Residue was purified by silica gel column chromatography (Wako Gel C-200, 100 g) and eluted with a mixed solvent of chloroform (98 parts) +methanol (2 parts) to give 4-acryloyl-2-[(5-acetamide)indole-3-yl]-1,4-benzothiazepine (3.0 g).

IR $\nu_{max}^{KBr}$(cm$^{-1}$): 3250, 1640. $^1$H-NMR(CDCl$_3$, 100 MHz)δ: 2.08, 2.12 (each 1.5H, each s), 3.50–5.80 (5H, m), 6.10–8.05 (12H, m), 9.08 (1H, br s). FD-MS (m/z): 391 (M+)

Experimental Example 10

The above-mentioned 4-acryloyl-2-[(5-acetamide) indole-3-yl]-1,4-benzothiazepine (3.0 g) and 4-benzyl piperidine (1.7 g) were dissolved in chloroform (30 ml) and methanol (5 ml) and the mixture was left to stand at room temperature for 24 hours. The solvent was distilled out under reduced pressure and thereafter residue was purified by silica gel column chromatography (Wako Gel C-200, 100 g) and eluted with a mixed solvent of chloroform (97 parts)+methanol (3 parts) to give 2-[(5-(acetamide) indole-3-yl]-4-[3-[1-(4-benzyl)-piperidinyl]propionyl]-2,3,4,5-tetrahydro-1,4-benzothiazepine (4.0 g) (compound (b)). This compound (1.0 g) was treated in the same manner as in Experimental Example 5 to obtain a hydrochloride ( 1.0 g ) in the form of powder.

IR $\nu_{max}^{KBr}$(cm$^{-1}$): 3400, 3250 (for hydrochloride) $^1$H-NMR(CDCl$_3$, 100 MHz)δ: 1.00–3.00 (13H, m), 2.07, 2.13 (each 1.5H, each s), 3.40–5.20 (7H, m), 6.65–8.10 (14H, m), 9.35 (1H, br s). FD-MS (m/z): 566 (M+)

Experimental Example 11

The above-mentioned 4-acryloyl-2-chloro-2,3,4,5-tetrahydro-1,4-benzothiazepine (1.0 g), geraniol (0.9 g) and zinc chloride (0.8 g) were reacted in the same manner as in Experimental Example 9 to give 4-acryloyl-2-geranyloxy-2,3,4,5-tetrahydro-1,4-benzothiazepine (1.0 g).

IR $\nu_{max}^{CHCl3}$( cm$^{-1}$): 1640 $^1$H-NMR(CDCl$_3$, 100 MHz)δ: 1.60 (3H, s), 1.65 (6H, s), 2.00 (4H, br s), 3.75–5.20 (9H, m), 5.40–5.80 (1H, m), 6.10–6.75 (2H, m), 7.10–7.35 (2H, m), 7.40–7.60 (2H, m). FD-MS ( m/z ): 371 ( M+)

Experimental Example 12

The above-mentioned 4-acryloyl-2-geranyloxy-2,3,4,5-tetrahydro-1,4-benzothiazepine (1.0 g) and 4-benzyl piperidine (0.62 g) were reacted in the same manner as in Experimental Example 10 to give 4-[3-[1-(4-benzyl) piperidinyl]propionyl]-2-geranyloxy-2,S,4,5-tetrahydro-1,4-benzothiazepine (1.3 g) (compound (c)).

This compound (1.1 g) was treated in the same manner as in Experimental Example 5 to obtain a hydrochloride (1.0 g) in the form of thick syrup.

IR $\nu_{max}^{CHCl3}$(cm$^{-1}$): 1640 (for hydrochloride). $^1$H-NMR(CDCl$_3$, 100 MHz)δ: 0.80–1.70 (SH, m), 1.58, 1.62, 1.68 (each 3H, each s), 1.80–2.10 (4H, br s), 2.30–3.00 (8H, m), 3.70–5.30 (11H, m), 7.05–7.35 (7H, m), 7.40–7.60 (2H, m). FD-MS (m/z): 546 (M+)

Experimental Example 13

The above-mentioned 4-acryloyl-2-chloro-7-methoxy-2,3,4,5-tetrahydro-1,4-benzothiazepine (2.3 g) and anisole (1.1 g) were dissolved in methylene chloride (50 ml) and stannic chloride (2.8 g) was added thereto and agitated at room temperature for 2 hours. To the reaction mixture water was added and extracted with chloroform. The chloroform phase was washed with a saturated saline solution and dried on sodium sulfate and thereafter the solvent was distilled out under reduced pressure. Residue was purified by silica gel column chromatography (Wako Gel C-200, 50 g) and eluted with a mixed solvent of n-hexane (70 parts)+ethyl acetate (30 parts) to give 4-acryloyl-2-[4-methoxyphenyl]-7-methoxy-2,3,4,5-tetrahydro-1,4-benzothiazepine (1.7 g).

IR $\nu_{max}^{CHCl3}$(cm$^{-1}$): 1640. $^1$H-NMR(CDCl$_3$, 100 MHz)δ: 3.81 (3H, s), 3.83 (3H, s), 3.60–5.45 (5H, m), 5.50–7.60 (10H, m). FD-MS (m/z): 355 (M+)

Experimental Example 14

The above-mentioned 4-acryloyl-2-(4-methoxyphenyl)-7-methoxy-2,3,4,5-tetrahydro-1,4-benzothiazepine (1.2 g) and 4-benzyl piperidine (0.95 g) were reacted in the same manner as in Experimental Example 5 to give 4-[3-[1-(4-benzyl) piperidinyl]propionyl]-2-(4-methoxyphenyl)-7-methoxy-2,3,4,5-tetrahydro-1,4-benzothiazepine (1.75 g) (compound (d)). This compound (1.2 g) was treated in the same manner as in Experimental Example 5 to obtain a hydrochloride (1.2 g) in the form of powder.

IR $\nu_{max}^{KBr}$(cm$^{-1}$): 3430 1640 (for hydrochloride) $^1$H-NMR(CDCl$_3$, 500 MHz)δ: 1.10–3.00 (15H, m), 3.80 (3H, s), 3.81 (3H, s), 3.70–5.21 (SH, m), 6.62–7.65 (12H, m). FD-MS (m/z): 530 (M+)

Experimental Example 15

The above-mentioned 4-bromoacetyl-2,3,4,5-tetrahydro-1,4-benzothiazepine (2.5 g) and sulfuryl chloride (1.5 g) were reacted in the same manner as in Experimental Example 7 to give 4-bromoacetyl-2-chloro-2,3,4,5-tetrahydro-1,4-benzothiazepmne (1.4 g). This compound (0.30 g), geraniol (0.30 g) and zinc chloride (0.26 g) were reacted in the same manner as in Experimental Example 9 to give 4-bromoacetyl-2-geranyloxy-2,3,4,5-tetrahydro-1,4-benzothiazepine (0.21 g). Then, this compound (0.21 g), 4-benzyl piperidine (O.11 g) and potassium carbonate (0.13 g) were reacted in the same manner as in Experimental Example 6 to give 4-[1-(4-benzyl) piperidinyl]acetyl-2-geranyloxy-2,3,4,5-tetrahydro-1,4-benzothiazepine (0.26 g).

IR $\nu_{max}^{CHCl3}$(cm$^{-1}$): 1640 . $^1$H-NMR(CDCl$_3$, 500MHz)δ:1.28–2.15 (11H, m), 2.48–3.40 (6H, m), 1.57 (3H, s), 1.64 (3H, s), 1.68 (3H, s), 3.80–5.30 (7H, m), 7.10–7.56 (9H, m). FD-MS (m/z): 532 (M+).

Experimental Example 16

The above-mentioned 4-bromoacetyl-2-chloro-2,3,4,5-tetrahydro-1,4-benzothiazepine (0.50 g), 5-

(acetamide)indole (1.0 g) and zinc chloride (0.78 g) were reacted in the same manner as in Experimental Example 9 to give 4-bromoacetyl-2-[(5-acetamide) indole-3-yl]-1,4-benzothiazepine (0.67 g). This compound (0.67 g), 4-benzyl piperidine (0.33 g) and potassium carbonate (0.40 g) were reacted in the same manner as in Experimental Example 6 to give 2-[(5-acetamide)indole-3-yl]-4-[1-(4-benzyl)piperidinyl]acetyl-2,3,4,5-tetrahydro-1,4-benzothiazepine (0.66 g).

IR $\nu_{max}^{CHCl_3}$(cm$^{-1}$): 3470, 1670, 1630. $^1$H-NMR(CDCl$_3$, 500 MHz)δ: 1.10–5.35 (18H, m), 2.13, 2.15 (each 1.5H, each s ), 6.80–7.95 (13H, m), 8.65 (1H, br s) 8.80 (1H, s). FD-MS (m/z): 552 (M+).

Experimental Example 17

The above-mentioned 4-bromoacetyl-2-chloro-7-methoxy-2,3,4,5-tetrahydro-1,4-benzothiazepine (0.19 g), anisole (0.07 g) end stannic chloride (0.17 g) were reacted in the same manner as in Experimental Example 13 to give 4-bromoacetyl-7-methoxy-2-(4-methoxyphenyl)-2,3,4,5-tetrahydro-1,4-benzothiazepine (0.17 g). This compound (0.1g), 4-benzyl piperidine (0.09 g) and potassium carbonate (0.11 g) were reacted in the same manner as in Experimental Example 6 to give 4-[1-(4-benzyl)piperidinyl]acetyl-7-methoxy-2-(4-methoxyphenyl)-2,3,4,5-tetrahydro-1,4-benzothiazepine (0.20 g).

IR $\nu_{max}^{CHCl_3}$(cm$^{-1}$): 1640. $^1$H-NMR( CDCl$_3$, 100 MHz )δ: 1.00–3.55 (13H, m), 3.80 (3H, s), 3.81 (3H, s), 3.70–5.45 (5H, m), 6.62–7.56 (12H, m). FD-MS (m/z): 516 (M+).

Experimental Example 18

The above-mentioned 4-[3-[1-(4-benzyl)piperidinyl]propionyl]-7-methoxy-2,3,4,5-tetrahydro-1,4-benzothiazepine (0.90 g) was dissolved in THF (50 ml) and aluminum lithium hydride (0.24 g) was added thereto at 0° C. and agitated at 0° C. for 2 hours. After an excess amount of aluminum lithium hydride was decomposed with sodium sulfate.10 hydrates, filtration was made with celite. After concentrating the resulting filtrate under reduced pressure, the concentrate was purified by silica gel column chromatography (Wako Gel C-200, 20 g) and eluted by a mixed solvent of chloroform (98 parts)+methanol (2 parts) to give 4-[3-[1-(4-benzyl)piperidinyl]propyl]-7-methoxy-2,S,4,5-tetrahydro-1,4-benzothiazepine (0.71 g).

IR $\nu_{max}^{CHCl_3}$(cm$^{-1}$): 1595, 1480. $^1$H-NMR (CDCl$_3$, 500 MHz)δ: 1.24–2.92(19H, m) 3.30–3.35 (2H, m), 3.78 (3H, s), 4.11 (2H, s), 6.65–7.45 (8H, m). FD-MS (m/z): 410 (M+).

Experimental Example 19

The above-mentioned 4-[3-[1-(4-benzyl)piperidinyl]propionyl]-2-(4-methoxyphenyl)-7-methoxy-2,3,4,5-tetrahydro-1,4-benzothiazepine (1.0 g) and aluminum lithium hydride (0.22 g) were reacted in the same manner as in Experimental Example 18 to give 4-[3-[1-(4-benzyl)piperidinyl]propyl]-2(4-methoxyphenyl)-7-methoxy-2,3,4,5-tetrahydro-1,4-benzothiazepine (0.46 g).

IR $\nu_{max}^{CHCl_3}$(cm$^{-1}$): 1610, 1595, 1510. $^1$H-NMR(CDCl$_3$, 500 MHz)δ: 1.24–2.93 ( 17H, m), 3.40–4.46 (SH, m), 3.79 (3H, s), 3.80 (3H, s), 6.69–7.50 (12H, m). FD-MS (m/z): 516 (M+).

Experimental Example 20

The above-mentioned 4-acryloyl-2-chloro-2,3,4,5-tetrahydro-1,4-benzothiazepine (0.20 g), methanol (0.1 ml) and stannic chloride (0.31 g) were reacted in the same manner as in Experimental Example 13 to give 4-acryloyl-2-methoxy-2,3,4,5-tetrahydro-1,4-benzothiazepine (0.19 g). This compound (0.18 g) and 4-benzyl piperidine (0.19 g) were reacted in the same manner as in Experimental Example 5 to give 4-[3-[1-(4-benzyl)piperidinyl]propionyl]-2-methoxy-2,3,4,5-tetrahydro-1,4-benzothiazepine (0.25 g).

IR $\nu_{max}^{CHCl_3}$(cm$^{-1}$): 1640. $^1$H-NMR(CDCl$_3$, 100 MHz)δ: 1.10–2.10 (7H, m), 2.40–2.95 (6H, m), 3.35 (3H, s), 3.65–5.10 (7H, m), 7.00–7.30 (7H, m), 7.35–7.55 (2H, m). FD-MS (m/z): 424 (M+).

(Preparation of a starting material, 7-methoxy-2,3,4,5-tetrahydro-1,4-benzothiazepine)

Preparation Example 1

2,5-Dihydroxy benzoic acid (50.0 g) was dissolved in acetonitrile (400 ml) and dimethyl sulfate (67.5 ml) and potassium carbonate (98.1 g) were added thereto and heated at reflux for 3 hours. Water was added to thereaction mixture and extracted with chloroform. The chloroform phase was washed with a saturated saline solution, thereafter dried on sodium sulfate and the solvent was distilled out under reduced pressure. The residue was purified by silica gel column chromatography (Wako Gel C-200, 200 g) and eluted by a mixed solvent of n-hexane (95 parts)+ethyl acetate (5 parts) to give methyl 2-hydroxy-5-methoxy benzoate (47.1 g).

IR $\nu_{max}^{CHCl_3}$(cm$^{-1}$): 3250, 1680, 1620. $^1$H-NMR(CDCl$_3$, 100 MHz)δ: 3.77 (3H, s), 3.94 (3H, s), 6.89 (1H, d, J=8.5 Hz), 7.06 (1H, dd, J=2.9 Hz, 8.5 Hz), 7.27 (1H, d, J=2.9 Hz), 10.27 (1H, s).

Preparation Example 2

The above-mentioned methyl 2-hydroxy-5-methoxy benzoate (47.4 g) was dissolved in dimethylformamide (400 ml) and 1,4-diazabicyclo[2,2]octane (43.8 g) and dimethylthiocarbamoyl chloride (48.00 g) were added thereto and agitated at room temperature for 20 hours. The reaction mixture was poured in a 10% hydrogen chloride solution (300 ml) and extracted with ethyl acetate. The ethyl acetate phase was washed with a saturated saline solution, dried on sodium sulfate and the solvent was distilled out under reduced pressure. The residue thus obtained was washed with a mixed solvent of n-hexane (2 parts)+ethyl acetate (1 part) to give methyl 2-[(dimethylamino)thiooxomethoxy]-5-methoxy benzoate (55.0 g).

mp 99.5°–100.5° C. IR $\nu_{max}^{CHCl_3}$(cm$^{-1}$): 1710, 1490. $^1$H-NMR(CDCl$_3$, 100 MHz)δ: 3.37 (3H, s), 3.45 (3H, s), 3.83 (6H, s), 7.02–7.09 (2H, m), 7.45–7.51 (1H, m)

Preparation Example 3

To the above-mentioned methyl 2-[(dimethylamino)thiooxomethoxy]-5-methoxy benzoate (20.0 g), diphenyl ether (100 ml) was added and heated at 265°–270° C. for 9 hours. After standing to cool, the reaction mixture was purified by silica gel column chromatography (Wako Gel C-200, 200 g) and eluted by a mixed solvent of n-hexane (65 parts)+ethyl acetate (35 parts) to give methyl 2-dimethylcarbamoylthio-5-methoxy benzoate (16.4 g).

mp 64.0°–65.0° C. IR $\nu_{max}^{CHCl_3}$(cm$^{-1}$): 1720, 1650, 1590 $^1$H-NMR(CDCl$_3$, 100 MHz)δ: 3.04 (6H, s), 3.83 (3H, s), 3.87 (3H, s), 7.00 (1H, dd, J=2.9 Hz, 8.5 Hz), 7.39 (1H, d, J=2.9 Hz), 7.42 (1H, d, J=8.5 Hz).

Preparation Example 4

The above-mentioned methyl 2-dimethylcarbamoylthio-5-methoxy benzoate (20.0 g) was dissolved in methanol (200 ml) and sodium methoxide (8.0 g) was added thereto and heated at reflux for 20 hours. The reaction mixture was poured in a 10% hydrogen chloride solution (300 ml) and extracted with ethyl acetate. The ethyl acetate phase was washed with a saturated saline solution, thereafter dried on sodium sulfate and the solvent was distilled out under reduced pressure. The residue thus obtained was purified by silica gel column chromatography (Wako Gel C-200, 200 g) and eluted by a mixed solvent of n-hexane (90 parts)+ethyl acetate (10 parts) to give methyl 2-mercapto-5-methoxy benzoate (11.0 g).

IR $\nu_{max}^{CHCl3}(cm^{-1})$: 1700 1590 1470. $^1$H-NMR(CDCl$_3$, 100 MHz)$\delta$: 3.80 (3H, s), 3.92 (3H, s), 4.47 (1H, s), 6.88 (1H, dd, J=3.0 Hz 8.5 Hz), 7.22 (1H, d, J=8.5 Hz), 7.51 (1H, d, J=3.0 Hz).

Preparation Example 5

The above-mentioned methyl 2-mercapto-5-methoxy benzoate (6.5 g) and 2-chloroethylamine hydrochloride (4.6 g) were dissolved in dimethylformamide (100 ml) and sodium methoxide (4.7 g) was added thereto under ice cooling and thereafter agitated at room temperature for 12 hours. The reaction mixture was poured in a 10% hydrogen chloride solution (100 ml) and extracted with chloroform. The chloroform phase was washed with a saturated saline solution, dried on sodium sulfate and thereafter the solvent was distilled out under reduced pressure to obtain a crude crystal. The crystal was washed with a mixed solvent of ethyl acetate (50 parts)+n-hexane (50 parts) to give 7-methoxy-5-oxo-2,3,4,5-tetrahydro-1,4-benzothiazepine (3.29).

mp 164.0°–166.0° C. IR $\nu_{max}^{CHCl3}(cm^{-1})$: 3350 1645 1450. $^1$H-NMR(CDCl$_3$, 100 MHz)$\delta$: 2.93–3.14 (2H, m), 3.24–3.48 (2H, m), 6.92 (1H, dd, J=2.9Hz, 8.5 Hz), 7.17 (1H, br s), 7.23 (1H, d, J=2.9Hz) 7.41 (1H, d, J=8.5 Hz). FD-MS (m/z): 209 (M+)

Preparation Example 6

Aluminum lithium hydride (2.739) and the above-mentioned 7-methoxy-5-oxo-2,3,4,5-tetrahydro-1,4-benzothiazepine (5.0 g) were added to THF (150 ml) under ice cooling and heated at reflux for 3 hours. After adding an excess amount of sodium sulfate.10 hydrates, a celite filtration was made. The resulting filtrate was concentrated to give 7-methoxy-2,3,4,5-tetrahydro-1,4-benzothiazepine (4.4 g).

IR $\nu_{max}^{CHCl3}(cm^{-1})$: 1240 1050. $^1$H-NMR(CDCl$_3$, 100 MHz)$\delta$: 2.62–2.88 (2H, m), 3.27–3.58 (2H, m), 3.79 (3H, s), 4.09 (2H, s), 6.59–7.00 (2H, m), 7.46 (1H, d, J=8.5 Hz). FD-MS (m/z): 195 (M+)

(Pharmacological Test)

Test Procedure (1)

The heart from a male rat weighing 300 to 380 g was isolated and perfusion was made under water-gauge pressure of 80 cm according to Langendorff's method. A Krebs-Henseleit bicarbonate solution (37° C., pH 7.4) containing 11 mM glucose, oxygenated with a mixed gas of 95% $O_2$+5% $CO_2$. Furthermore, the heart was compulsively driven by electrostimulation at 330 beats/min. After stabilizing for 10 minutes, perfusion was made for 10 minutes using the Krebs-Henseleit solution containing 5.5 mM calcium as calcium setting in which an amount of the test compound was dissolved. Thereafter, 0.5 ml of an aqueous solution containing 0.1 mg of adrenaline was poured into the perfusate as a trigger drug, and after 1 minute, 1 ml of an aqueous solution containing 10 mg caffeine was added therein. After additional 2 minutes, the heart was taken out to be put in a formaldehyde solution. The heart was fixed in the formaldehyde solution and then was cut horizontally at intervals of about 3 mm. Each of the cut blocks was dehydrated, defatted and embedded in paraffin, in due form, and then was sliced into a 3 to 4 $\mu$m thickness. The cut sample was stained by Heidenhain's iron hematoxylin stain method to make a preparation. With an optical microscope, a five-rating evaluation (−, ±, +, ++, +++) was made on the basis of the degree of myocardial necrosis. Where the ration of myocardial necrosis to the sectional area of the left ventricle of the heart was not more than 5%, i.e. (−) and (±), it was determined that there was a myocardial necrosis-inhibiting effect.

Test Procedure (2)

The heart from a male rat weighing 300 to 380 g was isolated and perfusion was made under water-gauge pressure of 80 cm according to Langendorff's method, under the same condition as in Test Procedure (1). A latex balloon was inserted in the left ventricle of the heart and used to measure both left ventricular pressure and heart rate. In this test, when the heart function had stabilized, perfusion was made for 10 minutes using the perfusate containing the compound to be tested, and change in the heart function was recorded. The value of heart rate (HR)×left ventricular pressure (LVP) was evaluated as an indication of heart function.

| Compounds to be tested | Concentration (M) | Case Numbers | Degree of Myocardial Necrosis* | Effect on Heart Function** (HR × LVP, Control = 100%) |
|---|---|---|---|---|
| Physiological saline | | 11 | +~++ | 100.2 ± 5.4 |
| Diltiazem Hydrochloride | 10-6 | 3 | +~++ | 35.9 ± 9.8 |
| Diltiazem Hydrochloride | 10-5 | 5 | ± | 10.4 ± 5.2 |
| Compound (a) | 10-6 | 3 | −~± | 101.1 ± 2.5 |
| Compound (b) | 10-6 | 3 | −~± | 92.3 ± 7.2 |
| Compound (c) | 10-6 | 3 | −~± | 96.5 ± 3.8 |
| Compound (d) | 10-6 | 3 | −~± | 96.0 ± 5.4 |

*Test Procedure (1)
**Test Procedure (2)

It can be seen from the above-mentioned test (1) that all Compounds (a)–(d) have a more potent effect of inhibiting myocardial tissue necrosis than does diltiazem hydrochloride (trade name: HERBESSER). In addition, as can be seen from Test (2), even in doses large enough to inhibit myocardial necrosis, Compounds (a)–(d) have little effect on the heart. For this reason, Compounds (a)–(d), as the effective ingredient of drugs for myocardial protection which inhibit myocardial necrosis, are effective substances capable of exhibiting an aimed pharmacological effect without inhibiting the heart function, in the field of drugs for the prevention of acute myocardial infarction or prevention of recurrence thereof.

We claim:

1. A 1,4-benzothiazepine derivative represented by the following Formula [I]:

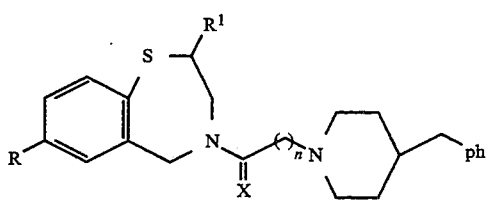

wherein each of substituent groups is defined as follows: R represents H or a $C_1$–$C_3$ lower alkoxy group; X represents O or $H_2$; n represents 1 or 2; $R^1$ represents H, a substituted phenyl group wherein the substituent group is OH or a $C_1$–$C_3$ lower alkoxy group,

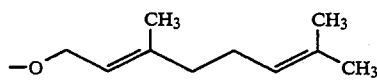

a $C_1$–$C_3$ lower alkoxy group or

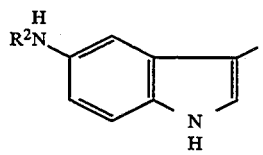

wherein $R^2$ represents a $C_1$–$C_3$ acyl group, and ph represents a phenyl group, or a pharmaceutically acceptable salt thereof.

2. A pharmaceutical composition for the prevention of myocardial infarction or for inhibiting myocardial necrosis comprising a myocardial necrosis-inhibiting effective amount of a 1,4-benzothiazepine derivative represented by the following Formula [I]:

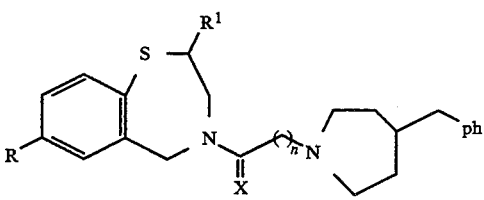

wherein each of substituent groups is defined as follows: R represents H or a $C_1$–$C_3$ lower alkoxy group; X represents O or $H_2$; n represents 1 or 2; $R^1$ represents H, a substituted phenyl group wherein the substituent group is OH or a $C_1$–$C_3$ lower alkoxy group,

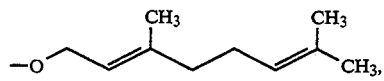

a $C_1$–$C_3$ lower alkoxy group or

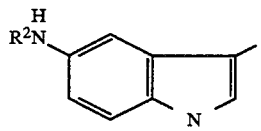

wherein $R^2$ represents a $C_1$–$C_3$ acyl group, and ph represents a phenyl group, or a pharmaceutically acceptable salt thereof, and a pharmaceutical carrier therefor.

3. A process for inhibiting myocardial necrosis in a human comprising administering to said human an effective amount of 1,4-benzothiazepine derivative having the following formula:

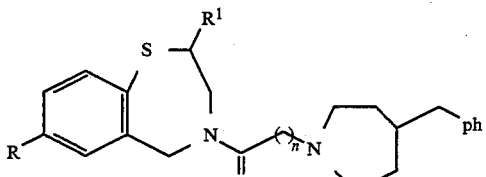

wherein each of substituent groups is defined as follows: R represents H or a $C_1$–$C_3$ lower alkoxy group; X represents O or $H_2$; n represents 1 or 2; $R^1$ represents H, a substituted phenyl group wherein the substituent group is OH or a $C_1$–$C_3$ lower alkoxy group,

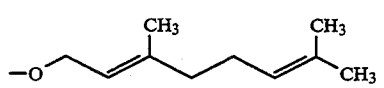

a $C_1$–$C_3$ lower alkoxy group or

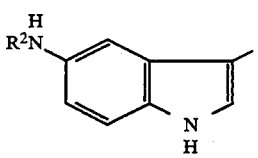

wherein $R^2$ represents a $C_1$–$C_3$ acyl group, and ph represents a phenyl group, or a pharmaceutically acceptable salt thereof.

4. The 1,4-benzothiazepine derivative according to claim 1 wherein R is H or a methoxy group.

5. The 1,4-benzothiazepine derivative according to claim 1 wherein $R^1$ is H, methoxyphenyl, geranyloxy, methoxy or (acetamide)indolyl groups.

6. The 1,4-benzothiazepine derivative according to claim 1 wherein R is H or methoxy and $R^1$ is H, methoxyphenyl, geranyloxy, methoxy or (acetamide)indolyl groups.

7. The 1,4-benzothiazepine derivative according to claim 1 wherein said derivative is 4-[3-[1-(4-benzyl) piperidinyl]propionyl]-7-methoxy-2,3,4,5-tetrahydro-1,4-benzothiazepine, 4-[1-(4-benzyl) piperidinyl]acetyl-7-methoxy-2,3,4,5-tetrahydro-1,4-benzothiazepine, 2-[5-(acetamide)indole-3-yl]-4-[3-[1-(4-benzyl) piperidinyl]propionyl]-2,3,4,5-tetrahydro-1,4-benzothiazepine,
4-[3-[1-(4-benzyl) piperidinyl]propionyl]-2-geranyloxy-2,3,4,5-tetrahydro-1,4-benzothiazepine,
4-[3-[1-(4-benzyl)piperidinyl]propionyl]-2-(4-methoxyphenyl)-7-methoxy-2,3,4,5-tetrahydro-1,4-benzothiazepine,
4-[1-(4-benzyl) piperidinyl]acetyl-2-geranyloxy-2,3,4,5-tetrahydro-1,4-benzothiazepine,
2-[5-(acetamide)indole-3-yl]-4-[1-(4-benzyl) piperidinyl]acetyl-2,3,4,5-tetrahydro-1,4-benzothiazepine,
4-[1-(4-benzyl) piperidinyl]acetyl-7-methoxy-2-(4-methoxyphenyl)2,3,4,5-tetrahydro-1,4-benzothiazepine,
4-[3-[1-(4-benzyl) piperidinyl]propyl]-7-methoxy-2,3,4,5-tetrahydro-1,4-benzothiazepine.
4-[3-[1-(4-benzyl)piperidinyl]propyl]-2-(4-methoxyphenyl)-7-methoxy-2,3,4,5-tetrahydro-1,4-benzothiazepine, or
4-[3-[1-(4-benzyl)piperidinyl]propionyl]-2-methoxy-2,3,4,5-tetrahydro-1,4-benzoyhiazepine.

8. The pharmaceutical composition according to claim 2 wherein R is H or a methoxy group.

9. The pharmaceutical composition according to claim 2 wherein $R^1$ is H, methoxyphenyl, geranyloxy, methoxy or (acetamide) indolyl groups.

10. The pharmaceutical composition according to claim 2 wherein R is H or a methoxy group and $R^1$ is H, methoxyphenyl, geranyloxy, methoxy or (acetamide) indolyl groups.

11. A process for preventing acute myocardial infarction in a human comprising administering to said human an effective amount of a 1,4-benzothiazepine derivative having the following formula:

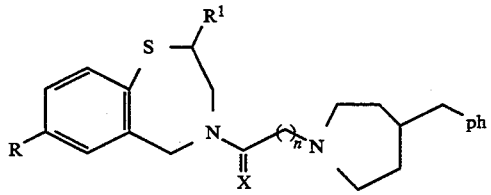

wherein each of substituent groups is defined as follows: R represents H or a $C_1$–$C_3$ lower alkoxy group; X represents O or $H_2$; n represents 1 or 2; $R^1$ represents H, a substituted phenyl group wherein the substituent group is OH or a $C_1$–$C_3$ lower alkoxy group,

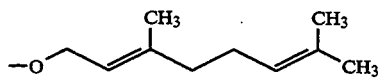

a $C_1$–$C_3$ lower alkoxy group or

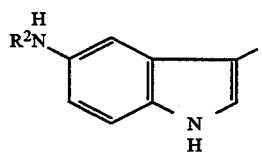

wherein $R^2$ represents a $C_1$–$C_3$ acyl group, and ph represents a phenyl group, or a pharmaceutically acceptable salt thereof.

12. The process according to claim 11 wherein $R^1$ in said 1,4-benzothiazepine derivative is H, methoxyphenyl, geranyloxy, methoxy or (acetamide) indolyl groups.

13. The process according to claim 11 wherein said 1,4-benzothiazepine derivative, R is H or methoxy and $R^1$ is H, methoxyphenyl, geranyloxy, methoxy or (acetamide) indolyl groups.

14. The process according to claim 11 wherein said 1,4-benzothiazepine derivative is
4-[3-[1-(4-benzyl) piperidinyl]propionyl]-7-methoxy-2,3,4,5-tetrahydro-1,4-benzothiazepine,
4-[1-(4-benzyl) piperidinyl]acetyl-7-methoxy-2,3,4,5-tetrahydro-1,4-benzothiazepine,
2-[5-(acetamide)indole-3-yl]-4-[3-[1-(4-benzyl) piperidinyl]propionyl]-2,3,4,5-tetrahydro-1,4-benzothiazepine,
4-[3-[1-(4-benzyl) piperidinyl]propionyl]-2-geranyloxy-2,3,4,5-tetrahydro-1,4-benzothiazepine,
4-[3-[1-(4-benzyl) piperidinyl]propionyl]-2-(4-methoxyphenyl)-7-methoxy-2,3,4,5-tetrahydro-1,4-benzothiazepine,
4-[1-(4-benzyl) piperidinyl]acetyl-2-geranyloxy-2,3,4,5-tetrahydro-1,4-benzothiazepine,
2-[5-(acetamide)indole-3-yl]-4-[1-(4-benzyl) piperidinyl]acetyl-2,3,4,5-tetrahydro-1,4-benzothiazepine,
4-[1-(4-benzyl) piperidinyl]acetyl-7-methoxy-2-4-methoxyphenyl)2,3,4,5-tetrahydro-1,4-benzothiazepine,
4-[3-[1-(4-benzyl) piperidinyl]propyl]-7-methoxy-2,3,4,5-tetrahydro-1,4-benzothiazepine,
4-[3-[1-(4-benzyl) piperidinyl]propyl]-2-(4-methoxyphenyl)-7-methoxy-2,3,4,5-tetrahydro-1,4-benzothiazepine.

15. The process according to claim 3 wherein R in said 1,4-benzothiazepine derivative is H or a methoxy group.

16. The process according to claim 3 wherein $R^1$ in said 1,4-benzothiazepine derivative is H, methoxyphenyl, geranyloxy, methoxy or (acetamide) indolyl groups.

17. The process according to claim 3 wherein said 1,4-benzothiazepine derivative, R is H or methoxy and $R^1$ is H, methoxyphenyl, geranyloxy, methoxy or (acetamide) indolyl groups.

18. The process according to claim 3 wherein said 1,4-benzothiazepine derivative is
4-[3-[1-(4-benzyl) piperidinyl]propionyl]-7-methoxy-2,3,4,5-tetrahydro-1,4-benzothiazepine,
4-[1-(4-benzyl) piperidinyl]acetyl-7-methoxy-2,3,4,5-tetrahydro-1,4-benzothiazepine,
2-[5-(acetamide)indole-3-yl]-4-[3-[1-(4-benzyl) piperidinyl]propionyl]-2,3,4,5-tetrahydro-1,4-benzothiazepine,
4-[3-[1-(4-benzyl) piperidinyl]propionyl]-2-geranyloxy-2,3,4,5-tetrahydro-1,4-benzothiazepine,
4-[3-[1-(4-benzyl) piperidinyl]propionyl]-2-(4-methoxyphenyl)-7-methoxy-2,3,4,5-tetrahydro-1,4-benzothiazepine,
4-[1-(4-benzyl) piperidinyl]acetyl-2-geranyloxy-2,3,4,5-tetrahydro-1,4-benzothiazepine,
2-[5-(acetamide)indole-3-yl]-4-[1-(4-benzyl) piperidinyl]acetyl-2,3,4,5-tetrahydro-1,4-benzothiazepine,
4-[1-(4-benzyl) piperidinyl]acetyl-7-methoxy-2-(4-methoxyphenyl)2,3,4,5-tetrahydro-1,4-benzothiazepine, 4-[3-[1-(4-benzyl) piperidinyl]propyl]-7-methoxy-2,3,4,5-tetrahydro-1,4-benzothiazepine, 4-[3-[1-(4-benzyl) piperidinyl]propyl]-2-(4-methoxyphenyl)-7-methoxy-2,3,4,5-tetrahydro-1,4-benzothiazepine, or 19. The process according to claim 11 wherein R in said 1,4-benzothiazepine derivative is H or a methoxy group.

* * * * *

UNITED STATES PATENT AND TRADEMARK OFFICE
CERTIFICATE OF CORRECTION

PATENT NO. : 5,416,,066
DATED : May 16, 1995
INVENTOR(S) : Noboru Kaneko, et al.

It is certified that error appears in the above-identified patent and that said Letters Patent is hereby corrected as shown below:

On the Title Page, Section [73]: "Kirin Brewery Co., Ltd." should read --Noboru Kaneko--
Column 2, line 24: "$CH_3$" should read --$C_3$--
Column 3, line 43: "live" should read --give--
Column 6, line 56: before "intravenously" insert --(e.g.--
Column 7, line 33: "(12.59)" should read --(12.5g)--
Column 9, line 44: after "3250" insert --, 1635--
Column 9, line 67: "S,4," should read --3,4,--
Column 10, lines 5 & 43: "(SH" should read --(5H--
Column 10, line 51: "benzothiazepmne" should read --benzothiazepine--
Column 11, line 45: "S,4," should read --3,4,--
Column 11, line 62: "(SH" should read --(5H--
Column 13, line 32: "(3.29)" should read --(3.2g)--
Column 13, line 40: "(2.739)" should read --(2.73g)--
Column 18, line 35, Claim 14: after "thiazepine" delete --.-- and insert --, or 4-[3-[1-(4-benzyl) piperidinyl] propionyl]-2-methoxy-2,3,4,5-tetrahydro-1,4-benzothiazepine.--
Column 20, line 2, Claim 18: after "or" insert --4-[3-[1-(4-benyzl) piperidinyl] propionyl]-2-methoxy-2,3,4,5-tetrahydro-1,4-benzothiazepine.--

Signed and Sealed this

Third Day of November, 1998

Attest:

BRUCE LEHMAN

Attesting Officer

Commissioner of Patents and Trademarks